(12) United States Patent
Lee et al.

(10) Patent No.: US 12,163,965 B2
(45) Date of Patent: Dec. 10, 2024

(54) METHODS OF CULTURING AND CHARACTERIZING ANTIBODY SECRETING CELLS

(71) Applicant: Emory University, Atlanta, GA (US)

(72) Inventors: Frances Eun-Hyung Lee, Atlanta, GA (US); Ignacio Sanz, Atlanta, GA (US); Doan C. Nguyen, Atlanta, GA (US)

(73) Assignee: Emory University, Atlanta, GA (US)

( * ) Notice: Subject to any disclaimer, the term of this patent is extended or adjusted under 35 U.S.C. 154(b) by 631 days.

(21) Appl. No.: 17/405,918

(22) Filed: Aug. 18, 2021

(65) Prior Publication Data

US 2021/0382066 A1  Dec. 9, 2021

Related U.S. Application Data

(62) Division of application No. 15/992,174, filed on May 30, 2018, now Pat. No. 11,125,757.

(60) Provisional application No. 62/511,468, filed on May 26, 2017.

(51) Int. Cl.
| | | |
|---|---|---|
| *C12N 5/02* | (2006.01) | |
| *C12N 5/16* | (2006.01) | |
| *G01N 33/50* | (2006.01) | |
| *G01N 33/68* | (2006.01) | |

(52) U.S. Cl.
CPC ......... *G01N 33/6854* (2013.01); *C12N 5/163* (2013.01); *G01N 33/5091* (2013.01)

(58) Field of Classification Search
None
See application file for complete search history.

(56) References Cited

U.S. PATENT DOCUMENTS

| 4,259,447 | A | 5/1981 | Hafeli |
| 11,125,757 | B2 | 9/2021 | Lee |
| 2002/0072089 | A1 | 6/2002 | Holtzman |
| 2005/0272152 | A1 | 12/2005 | Xu |
| 2011/0076253 | A1 | 3/2011 | Snyder |
| 2013/0295672 | A1 | 11/2013 | Planelles |
| 2014/0205563 | A1 | 7/2014 | Maguire |
| 2018/0179495 | A1 | 6/2018 | Lee |

FOREIGN PATENT DOCUMENTS

| EP | 2540820 | 2/2013 |
| EP | 2574666 | 3/2013 |
| WO | 1998010056 | 3/1998 |
| WO | 2001055350 | 8/2001 |
| WO | 2006005153 | 1/2006 |
| WO | 2006015373 | 2/2006 |
| WO | 2006088972 | 8/2006 |
| WO | 2014132032 | 9/2014 |
| WO | 2014146074 | 9/2014 |
| WO | 2014152832 | 9/2014 |
| WO | 2016201077 | 12/2016 |

OTHER PUBLICATIONS

Arora, Cell Culture Media: A Review,Mater Methods 2013, 3:175, available at https://www.labome.com/method/Cell-Culture-Media-A-Review.html.
Avery et al. BAFF selectively enhances the survival of plasmablasts generated from human memory B cells, J. Clin. Invest. 112:286-297 (2003).
Cassese et al. Plasma Cell Survival Is Mediated by Synergistic Effects of Cytokines and Adhesion-Dependent Signals, The Journal of Immunology, 2003, 171: 1684-1690.
Cocco et al. In Vitro Generation of Long-lived Human Plasma Cells, The Journal of Immunology, 2012, 189: 5773-5785.
Dilillo et al. Maintenance of Long-Lived Plasma Cells and Serological Memory Despite Mature and Memory B Cell Depletion during CD20 Immunotherapy in Mice, The Journal of Immunology, 2008, 180: 361-371.
Extended European Search Report for EP Application No. 16808268.3 dated Nov. 30, 2018.
Garimalla et al. Differential transcriptome and development of human peripheral plasma cell subsets, JCI Insight. 2019, 4(9):e126732.
Gomez et al. Basophils Support the Survival of Plasma Cells in Mice, The Journal of Immunology, 2010, 185: 7180-7185.
Halliley et al. Long-Lived Plasma Cells Are Contained within the CD19-CD38hiCD138+ Subset in Human Bone Marrow, 2015, Immunity 43, 132-145.
Jourdan et al. IL-6 supports the generation of human long-lived plasma cells in combination with either April or stromal cell-soluble factors, Leukemia (2014) 28, 1647-1656.
Lanzavecchia, Long-term culture of normal and malignant plasma cells, available at http://www.irb.usi.ch/long-term-culture-normal-and-malignant-plasma-cells, printed 2016.
Manz et al. Lifetime of plasma cells in the bone marrow, Nature, 1997, 388(6638):133-4.
Matsuda et al. A proliferation-inducing ligand sustains the proliferation of human naïve (CD27negative) B cells and mediates their differentiation into long-lived plasma cells in vitro via transmembrane activator and calcium modulator and cyclophilin ligand interactor and B-cell mature antigen, Cellular Immunology 295 (2015) 127-136.
Mesin et al. Long-Lived Plasma Cells from Human Small Intestine Biopsies Secrete Immunoglobulins for Many Weeks In Vitro, The Journal of Immunology, 2011, 187: 2867-2874.
Nguyen et al. Factors of the bone marrow microniche that support human plasma cell survival and immunoglobulin secretion, Nat Commun. 2018, 9(1):3698.

(Continued)

*Primary Examiner* — Michail A Belyavskyi
(74) *Attorney, Agent, or Firm* — Emory Patent Group

(57) ABSTRACT

This disclosure relates to methods of culturing and characterizing antibody secreting cells. In certain embodiments, this disclosure relates to methods of isolating antibody secreting cells, e.g., long lived plasma cells, replicating the isolated cells in growth media disclosed herein, and determining the nucleic acids sequences in the cells that encode the produced antibodies.

7 Claims, 5 Drawing Sheets
Specification includes a Sequence Listing.

(56) References Cited

OTHER PUBLICATIONS

Nguyen et al. Extracellular vesicles from bone marrow-derived mesenchymal stromal cells support ex vivo survival of human antibody secreting cells, Journal of Extracellular Vesicles, 2018 vol. 7, 1463778, 14 pages.
Palumbo et al. Multiple Myeloma, N Engl J Med, 2011;364:1046-60.
Radbruch et al. Competence and competition: the challenge of becoming a long-lived plasma cell, Nat Rev Immunol. 2006, 6(10):741-50.
Roldan et al. VLA-4-Fibronectin Interaction Is Required for the Terminal Differentiation of Human Bone Marrow Cells Capable of Spontaneous and High Rate Immunoglobulln Secretion, J Exp Med. 1992, 175(6): 1739-1747.
Shapiro et al. Blimp-1 is required for maintenance of long-lived plasma cells in the bone marrow, J Exp Med. 2005, 202(11): 1471-1476.
Spencer et al. Direct measurement of local oxygen concentration in the bone marrow of live animals, Nature. 2014, 508(7495): 269-273.
Wols et al. The Role of Bone Marrow-Derived Stromal Cells in the Maintenance of Plasma Cell Longevity, The Journal of Immunology, 2002, 169: 4213-4221.
Wols et al. The effects of microenvironment and internal programming on plasma cell survival, International Immunology, 2007, vol. 19, No. 7, pp. 837-846.

SEQUENCE LISTING

```
<160> NUMBER OF SEQ ID NOS: 3

<210> SEQ ID NO 1
<211> LENGTH: 250
<212> TYPE: PRT
<213> ORGANISM: Artificial
<220> FEATURE:
<223> OTHER INFORMATION: Synthetic

<400> SEQUENCE: 1
```

```
Met Pro Ala Ser Ser Pro Phe Leu Leu Ala Pro Lys Gly Pro Gly
1               5                   10                  15

Asn Met Gly Gly Pro Val Arg Glu Pro Ala Leu Ser Val Ala Leu Trp
            20                  25                  30

Leu Ser Trp Gly Ala Ala Leu Gly Ala Val Ala Cys Ala Met Ala Leu
        35                  40                  45

Leu Thr Gln Gln Thr Glu Leu Gln Ser Leu Arg Arg Glu Val Ser Arg
50                  55                  60

Leu Gln Gly Thr Gly Pro Ser Gln Asn Gly Glu Gly Tyr Pro Trp
65              70                  75                  80

Gln Ser Leu Pro Glu Gln Ser Ser Asp Ala Leu Glu Ala Trp Glu Asn
                85                  90                  95

Gly Glu Arg Ser Arg Lys Arg Ala Val Leu Thr Gln Lys Gln Lys
            100                 105                 110

Lys Gln His Ser Val Leu His Leu Val Pro Ile Asn Ala Thr Ser Lys
        115                 120                 125

Asp Asp Ser Asp Val Thr Glu Val Met Trp Gln Pro Ala Leu Arg Arg
        130                 135                 140

Gly Arg Gly Leu Gln Ala Gln Gly Tyr Gly Val Arg Ile Gln Asp Ala
145                 150                 155                 160

Gly Val Tyr Leu Leu Tyr Ser Gln Val Leu Phe Gln Asp Val Thr Phe
                165                 170                 175

Thr Met Gly Gln Val Val Ser Arg Glu Gly Gln Gly Arg Gln Glu Thr
            180                 185                 190

Leu Phe Arg Cys Ile Arg Ser Met Pro Ser His Pro Asp Arg Ala Tyr
        195                 200                 205

Asn Ser Cys Tyr Ser Ala Gly Val Phe His Leu His Gln Gly Asp Ile
    210                 215                 220

Leu Ser Val Ile Ile Pro Arg Ala Arg Ala Lys Leu Asn Leu Ser Pro
225                 230                 235                 240

His Gly Thr Phe Leu Gly Phe Val Lys Leu
                245                 250
```

<210> SEQ ID NO 2
<211> LENGTH: 212
<212> TYPE: PRT
<213> ORGANISM: Artificial
<220> FEATURE:
<223> OTHER INFORMATION: Sytnhetic construct

<400> SEQUENCE: 2

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110
```

```
Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
                180                 185                 190

Leu Ile Leu Arg Ser Phe Lys Glu Phe Leu Gln Ser Ser Leu Arg Ala
                195                 200                 205

Leu Arg Gln Met
    210

<210> SEQ ID NO 3
<211> LENGTH: 135
<212> TYPE: PRT
<213> ORGANISM: Artificial
<220> FEATURE:
<223> OTHER INFORMATION: Synthetic construct

<400> SEQUENCE: 3

Cys Glu Ser Ser Lys Glu Ala Leu Ala Glu Asn Asn Leu Asn Leu Pro
1               5                   10                  15

Lys Met Ala Glu Lys Asp Gly Cys Phe Gln Ser Gly Phe Asn Glu Glu
                20                  25                  30

Thr Cys Leu Val Lys Ile Ile Thr Gly Leu Leu Glu Phe Glu Val Tyr
            35                  40                  45

Leu Glu Tyr Leu Gln Asn Arg Phe Glu Ser Ser Glu Glu Gln Ala Arg
            50                  55                  60

Ala Val Gln Met Ser Thr Lys Val Leu Ile Gln Phe Leu Gln Lys Lys
65                  70                  75                  80

Ala Lys Asn Leu Asp Ala Ile Thr Thr Pro Asp Pro Thr Thr Asn Ala
                85                  90                  95

Ser Leu Leu Thr Lys Leu Gln Ala Gln Asn Gln Trp Leu Gln Asp Met
            100                 105                 110

Thr Thr His Leu Ile Leu Arg Ser Phe Lys Glu Phe Leu Gln Ser Ser
            115                 120                 125

Leu Arg Ala Leu Arg Gln Met
            130                 135
```

METHODS OF CULTURING AND CHARACTERIZING ANTIBODY SECRETING CELLS

CROSS-REFERENCE TO RELATED APPLICATIONS

This application is a division of U.S. application Ser. No. 15/992,174 filed May 30, 2018, which claims the benefit of U.S. Provisional Application No. 62/511,468 filed May 26, 2017. The entirety of each of these applications is hereby incorporated by reference for all purposes.

STATEMENT REGARDING FEDERALLY FUNDED RESEARCH

This invention was made with government support under 1R01AI121252, 1P01AI125180, and P01A1078907 awarded by the National Institutes of Health. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 17091US_ST25.txt. The text file is 6 KB, was created on May 29, 2018 and is being submitted electronically via EFS-Web.

BACKGROUND

Human long-lived plasma cells (LLPCs) are responsible for the long-term maintenance of protective serum antibodies. However, the maintenance of LLPCs remain poorly understood. Plasma cells readily die when removed from their in vivo surrounding. Thus, there is a need to identify in vitro methods of inducing the replication or prolonging the survival of cells capable of producing antibodies.

Roldan et al. report VLA-4-fibronectin interaction is required for the terminal differentiation of human bone marrow cells capable of spontaneous and high rate immunoglobulin secretion. J Exp Med, 1992, 175(6):1739-47.

Minges Wols et al. report the role of bone marrow-derived stromal cells in the maintenance of plasma cell longevity. J Immunol, 2002, 169, 4213-4221.

Cassese et al. report plasma cell survival is mediated by synergistic effects of cytokines and adhesion-dependent signals. J Immunol, 2003, 171, 1684-1690.

Mesin et al. report long-lived plasma cells from human small intestine biopsies secrete immunoglobulins for many weeks in vitro. J Immunol, 2011, 187(6):2867-74.

Spencer et al. report the direct measurement of local oxygen concentration in the bone marrow of live animals. Nature, 2014, 508(7495):269-73.

Hallily et al. report long-lived plasma cells are contained within the CD19(−) CD38(hi)CD138(+) subset in human bone marrow. Immunity, 2015, 43(1):132-45.

WO 2016/201077 reports the use of MSCs for culturing cells.

References cited herein are not an admission of prior art.

SUMMARY

This disclosure relates to methods of culturing and characterizing cells such as antibody secreting cells. In certain embodiments, this disclosure relates to methods of isolating antibody secreting cells, e.g., long lived plasma cells, replicating the isolated cells in growth media disclosed herein, and determining the nucleic acids sequences in the cells that encode the produced antibodies.

In certain embodiments, this disclosure relates to methods of sequencing a nucleic acid of antibodies that specifically bind to an antigen comprising: isolating antibody secreting cells from a sample, providing separated single antibody secreting cells in a plurality of separate areas; mixing or culturing the separated single antibody secreting cells in the plurality of separated areas on a growth media disclosed herein such as a growth media with secretions of allogeneic mesenchymal stromal/stem cells and exogenously added A-proliferation-inducing ligand (APRIL) under conditions such that separated single antibody secreting cells replicate providing replicated homogenous antibody secreting cells in separate areas; identifying cells that produce antibodies that specifically bind to the antigen; and sequencing a nucleic acid that encodes the antibody in the replicated homogenous antibody secreting cells that bind the antigen.

In certain embodiments, nucleic acid sequencing is the DNA or RNA that encodes the heavy chain or light chain of the antibodies or the variable region of the heavy chain of the antibody and/or the variable region of the light chain of the antibody produced by the replicated homogenous antibody secreting cells.

In certain embodiments, identifying cells that produce antibodies that specifically bind to the antigen can be accomplished by testing the replicated homogenous antibody secreting cells for specific binding to an antigen. In certain embodiments, identifying cells that produce antibodies that specifically bind to the antigen can be accomplished by mixing the produced antibodies with an antigen comprising a label, e.g., conjugated radioactive or fluorescent tag, or the antigen may be fixed to a solid surface and antibody binding to the solid surface may be detected or measured.

In certain embodiments, the disclosure relates to quantifying the amount of antibody secreting cells in a sample that specifically bind to the antigen.

In certain embodiments, mixing or culturing the separated single antibody secreting cells in the plurality of areas with secretions of allogeneic mesenchymal stromal/stem cells and exogenously added A-proliferation-inducing ligand (APRIL) is under hypoxic conditions.

In certain embodiments, separated single antibody secreting cells in the plurality of separated areas produce antibodies that bind different antigens.

In certain embodiments, the sample is blood, bone marrow, or product derived therefrom.

In certain embodiments, isolating antibody secreting cells is accomplished by fluorescence activated cell sorting or the use of positive or negative separation of the cells by beads or magnetic beads that bind surface markers on the antibody secreting cells followed by suspending of the cells in a composition or solution. In certain embodiments, isolating antibody secreting cells is accomplished by separation of the composition or solution into separate areas, e.g., wells, vial, or test tubes, provides for about or less than one cell per separate area.

In certain embodiments, the antibody secreting cells have a cell surface profile of CD19+, CD27hi, and CD38hi.

In certain embodiments, the isolated cells are long-lived plasma cells, wherein the antibody secreting cells have a cell surface profile of CD19(−), CD38(hi), and CD138(+).

In certain embodiments, the cells producing antibodies that specifically bind an antigen that is a vaccine antigen or an antigen indicative of a previous antimicrobial infection, such as a viral, bacterial, fungal, or parasitic infection.

In certain embodiments, this disclosure relates to methods of identifying cells that produce antibodies that bind to an antigen comprising: isolating antibody secreting cells from a sample; mixing or culturing the isolated antibody secreting cells with secretions of allogeneic mesenchymal stromal/stem cells and exogenously added A-proliferation-inducing ligand (APRIL) under conditions such that isolated antibody secreting cells replicate providing replicated antibody secreting cells; and testing the replicated antibody secreting cells for specific binding to an antigen of an antibody derived from the replicated antibody secreting cells to identifying replicated antibody secreting cells that produce antibodies that bind to the antigen.

In certain embodiments, this disclosure relates to methods of identifying cells that produce antibodies that bind to an antigen comprising: isolating antibody secreting cells from a sample, providing separated single antibody secreting cells in a plurality of separate areas; mixing or culturing the separated single antibody secreting cells in the plurality of separate areas with secretions of allogeneic mesenchymal stromal/stem cells and exogenously added A-proliferation-inducing ligand (APRIL) under conditions such that separated single antibody secreting cells replicate providing replicated homogenous antibody secreting cells; and testing the replicated antibody secreting cells for specific binding to an antigen of an antibody derived from the replicated homogenous antibody secreting cells to identifying replicated homogenous antibody secreting cells that produce antibodies that bind to the antigen.

In certain embodiments, the disclosure relates to methods of determining the effectiveness of a vaccination comprising: administering a vaccine to a subject that results in the existence or production of a vaccine antigen in the subject; isolating antibody secreting cells from a sample, providing isolated antibody secreting cells, wherein the isolated antibody secreting cells produce antibodies that bind different antigens; mixing or culturing the isolated single antibody secreting cells with secretions of allogeneic mesenchymal stromal/stem cells and exogenously added A-proliferation-inducing ligand (APRIL) under conditions such that isolated single antibody secreting cells replicate providing replicated antibody secreting cells; and testing the replicated antibody secreting cells for specific binding to the vaccine antigen of an antibody derived from the replicated antibody secreting cells to identifying replicated antibody secreting cells that produce antibodies that bind to the vaccine antigen.

In certain embodiments, the disclosure relates to methods of determining the effectiveness of a vaccination comprising administering a vaccine to a subject that results in the existence or production of a vaccine antigen in the subject; isolating antibody secreting cells from a sample, providing isolated antibody secreting cells; mixing the isolated antibody secreting cells with secretions of allogeneic mesenchymal stromal/stem cells and exogenously added A-proliferation-inducing ligand (APRIL) under conditions such that isolated antibody secreting cells replicate providing replicated antibody secreting cells; and identifying replicated antibody secreting cells that produce antibodies that bind to the vaccine antigen.

In certain embodiments, the disclosure relates to methods of determining the effectiveness of a vaccination comprising: administering a vaccine to a subject that results in the existence or production of a vaccine antigen in the subject; isolating antibody secreting cells from a sample, providing separated single antibody secreting cells in a plurality of separate areas, wherein the separated single antibody secreting cells in plurality of areas produce antibodies that bind different antigens; mixing or culturing the separated single antibody secreting cells with secretions of allogeneic mesenchymal stromal/stem cells and exogenously added A-proliferation-inducing ligand (APRIL) under conditions such that separated single antibody secreting cells replicate providing replicated homogenous antibody secreting cells; and testing the replicated homogenous antibody secreting cells for specific binding to the vaccine antigen of an antibody derived from the replicated homogenous antibody secreting cells; to identifying replicated homogenous antibody secreting cells that produce antibodies that bind to the vaccine antigen.

In certain embodiments, time between administering the vaccine and isolating the antibody secreting cells from the sample is at least one year or two years or more. In certain embodiments, time between administering the vaccine and isolating the antibody secreting cells from the sample is at least three or four years or more. In certain embodiments, time between administering the vaccine and isolating the antibody secreting cells from the sample is at least six or seven years or more. In certain embodiments, time between administering the vaccine and isolating the antibody secreting cells from the sample is at least eight or nine years or more. In certain embodiments, time between administering the vaccine and isolating the antibody secreting cells from the sample is at least ten or fifteen years or more.

In certain embodiments, the disclosure relates to methods of producing a hybridoma that produces antibodies that bind to an antigen comprising: isolating antibody secreting cells from a sample providing separated single antibody secreting cells in a plurality of separate areas, mixing the separated single antibody secreting cells with secretions of allogeneic mesenchymal stromal/stem cells and exogenously added A-proliferation-inducing ligand (APRIL) under conditions such that separated single cells replicate providing replicated homogenous antibody secreting cells; and identifying homogenous antibody secreting cells that produce antibodies that specifically bind to the antigen; and fusing an homogenous antibody secreting cell identified to produce antibodies that specifically bind the antigen with an immortalized cell providing hybridoma cells that produce antibodies that specifically bind to the antigen.

In certain embodiments, this disclosure relates to methods of producing a hybridoma that produces antibodies that bind to an antigen comprising: isolating antibody secreting cells from a sample using fluorescence activated cell sorting, providing separated single antibody secreting cells in a plurality of separate areas; mixing or culturing the separated single antibody secreting cells with secretions of allogeneic mesenchymal stromal/stem cells and exogenously added A-proliferation-inducing ligand (APRIL) under conditions such that separated single cells replicate providing replicated homogenous antibody secreting cells; and testing the replicated homogenous antibody secreting cells for specific binding to an antigen of an antibody derived from the replicated homogenous antibody secreting cells to identify homogenous antibody secreting cells that produce antibodies that specifically bind to the antigen; and fusing an homogenous antibody secreting cell identified to produce antibodies that specifically bind the antigen with an immortalized cell providing hybridoma cells that produce antibodies that specifically bind to the antigen.

In certain embodiments, the disclosure relates to methods of determining the efficacy of an autoimmune therapy comprising: administering an autoimmune drug to a subject diagnosed with an autoimmune disease; isolating antibody secreting cells from a sample of the subject, providing isolated antibody secreting cells; mixing the isolated antibody secreting cells with secretions of allogeneic mesenchymal stromal/stem cells and exogenously added A-proliferation-inducing ligand (APRIL) under conditions such that isolated antibody secreting cells replicate providing replicated antibody secreting cells; identifying replicated antibody secreting cells that produce auto-antibodies that specifically bind to an autoimmune antigen associated with the diagnosed autoimmune disease; quantifying an amount of auto-antibodies or cells that produce auto-antibodies in the sample; and correlating the amount to the efficacy of the autoimmune therapy.

In certain embodiments, the disclosure relates to methods of determining the efficacy of an autoimmune therapy comprising: administering an autoimmune drug to a subject diagnosed with an autoimmune disease; isolating antibody secreting cells from a sample of the subject, providing separated single antibody secreting cells in a plurality of separate areas; mixing the separated single antibody secreting cells with secretions of allogeneic mesenchymal stromal/ stem cells and exogenously added A-proliferation-inducing ligand (APRIL) under conditions such that separated single antibody secreting cells replicate providing replicated homologous antibody secreting cells; identifying replicated homologous antibody secreting cells that produce auto-antibodies that specifically bind to an autoimmune antigen associated with the diagnosed autoimmune disease; quantifying an amount of auto-antibodies or cells that produce auto-antibodies in the sample; and correlating the amount to the efficacy of the autoimmune therapy.

In certain embodiments, the autoimmune drug is an anti-CD20 antibody. In certain embodiments, the sample is from subject is being treated for, diagnosed with, at risk of, exhibiting symptoms of an autoimmune disease. In certain embodiments, the subject has had therapeutic B cell depletion therapy, e.g. prior administration of therapeutic anti-CD20 antibodies, such as rituximab, ocrelizumab, obinutuzumab, and ofatumumab.

DETAILED DISCUSSION

Figure 1A:
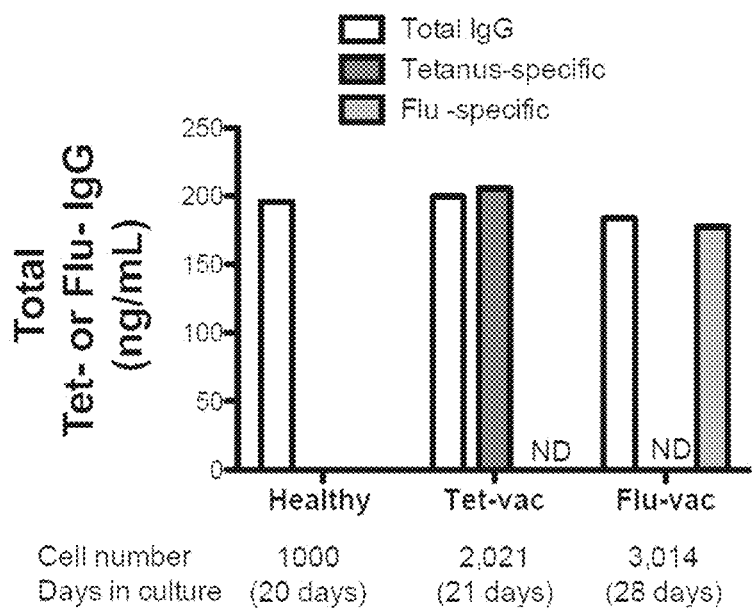
FIG. 1A shows data on culture supernatants of circulating ASC (CD19+CD27hi CD38hi) from 3 healthy adults at steady state, post-tetanus, or post-influenza (TIV) vaccination. Total IgG, tetanus-specific IgG, and influenza-specific IgG measured from total ASC 1,000, 2021, and 3014 ASC per well in 20, 21, and 28 day cultures respectively.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

The term "mesenchymal stromal cells" refers to the subpopulation of fibroblast or fibroblast-like nonhematopoietic cells with properties of plastic adherence and capable of in vitro differentiation into cells of mesodermal origin which may be derived from bone marrow, adipose tissue, umbilical cord (Wharton's jelly), umbilical cord perivascular cells, umbilical cord blood, amniotic fluid, placenta, skin, dental pulp, breast milk, and synovial membrane, e.g., fibroblasts or fibroblast-like cells with a clonogenic capacity that can differentiate into several cells of mesodermal origin, such as adipocytes, osteoblasts, chondrocytes, skeletal myocytes, or visceral stromal cells. The term, "mesenchymal stem cells" refers to the cultured (self-renewed) progeny of primary mesenchymal stromal cell populations. Mesenchymal stromal/stem cells (MSCs) refers to mesenchymal stromal and/or mesenchymal stem cells.

Bone marrow derived mesenchymal stromal cells are typically expanded ex vivo from bone marrow aspirates to confluence. Certain mesenchymal stromal/stem cells (MSCs) share a similar set of core markers and properties. Certain mesenchymal stromal/stem cells (MSCs) may be defined as positive for CD105, CD73, and CD90 and negative for CD45, CD34, CD14 or CD11b, CD79α or CD19, and HLA-DR surface markers, and have the ability to adhere to plastic. See Dominici et al. Minimal criteria for defining multipotent mesenchymal stromal cells. The International Society for Cellular Therapy position statement. Cryotherapy, 2006, 8(4):315-7.

Plasma cells (PCs) in human BM express high amounts of CD38. Long lived plasma cells can be obtained from human bone marrow cells, e.g., from iliac crest aspirates. Cells may be separated by flow cytometry. One can us FACS to remove lymphocytes having CD3 or CD14 expression (non-T cells, non-monocytes) and IgD cells (to eliminate late transitional and naive B cells). The remaining cells may be divided remove CD19 cell populations and subsequently obtained by the expression of both CD138 and CD38. In certain embodiments, antibody secreting cells such as ACSs or PC provide immunoglobulin secretion of at or more than 100, 125, 150 or 167±23 pg/cell/day.

The term "fluorescence-activated cell sorting" or "FACS" refers to a method of sorting a mixture of cells into two or more areas, typically one cell at a time, based upon the fluorescent characteristics of each cell. It is typically accomplished by applying an electrical charge and separating by movement through an electrostatic field. Fluorescent antibodies with epitopes to cell surface markers can be mixed with cells to mark the cells or cells can be transfected with fluorescent probes or molecular beacons that bind to mRNA. Typically, in FACS, a vibrating mechanism causes a stream of cells to break into individual droplets. Just prior to droplet formation, cells in a fluid pass through an area for measuring fluorescence of the cell. An electrical charging mechanism is configured at the point where the stream breaks into droplets. Based on the fluorescence intensity measurement, a respective electrical charge is imposed on the droplet as it breaks from the stream. The charged droplets then move through an electrostatic deflection system that diverts droplets into areas based upon their relative charge. In some systems, the charge is applied directly to the stream, and the droplet breaking off retains charge of the same sign as the stream. In other systems, a charge is provided on a conduit inducing an opposite charge on the droplet.

"Fibronectin" refers to either plasma insoluble fibronectin typically produced by fibroblasts, e.g., in an extracellular matrix, and plasma soluble fibronectin produced in the liver by hepatocytes sometimes referred to as "cold-insoluble globulin" which is a protein component of blood plasma. Fibronectin exists as a protein dimer, consisting of two monomers linked near the C-terminus by a pair of disulfide bonds. A typical fibronectin contains 12 type I modules, 2 type II modules, and 15-17 type III modules. The number of modules varies based on alternative gene splicing. There are two alternatively spliced segments in fibronectin due to alternative exon usage: extra domain A (EDA) located between the 11th and 12th of type III modules, and extra domain B (EDB) between the seventh and eighth type III modules. Plasma fibronectin typically lacks EDA and EDB sequences.

In certain embodiments, a growth medium disclosed herein comprises exogenously added fibronectin, fragment, or variant thereof. In certain embodiments, fibronectin is in the growth medium at a concentration of greater than $0.001 \times 10^{-3}\%$, $0.002 \times 10^{-3}\%$, $0.003 \times 10^{-3}\%$, $0.004 \times 10^{-3}\%$, $0.005 \times 10^{-3}\%$, $0.007 \times 10^{-3}\%$, $0.010 \times 10^{-3}\%$, $0.020 \times 10^{-3}\%$, $0.030 \times 10^{-3}\%$, $0.050 \times 10^{-3}\%$, $0.10 \times 10^{-3}\%$, $0.20 \times 10^{-3}\%$, $0.30 \times 10^{-3}\%$, $0.50 \times 10^{-3}\%$, $1.0 \times 10^{-3}\%$, $1.5 \times 10^{-3}\%$, $2.0 \times 10^{-3}\%$, 0.001%, 0.002%, 0.003%, 0.004%, 0.005%, 0.007%, 0.010%, 0.020%, 0.030%, 0.050%, 0.10%, 0.20%, 0.30%, 0.50%, 1.0%, 1.5%, 2.0%, by weight.

The protein "APRIL" refers to tumor necrosis factor superfamily member 13, which is a ligand for B-cell maturation antigen, a member of the tumor necrosis factor (TNF) receptor family. In certain embodiments, a growth medium disclosed herein comprises exogenously added APRIL, fragment, or variant thereof. In certain embodiments, the variant has greater than 30, 40, 50, 60, 70, 80, 85, 90, 95, 96, 97, 98 or 99% identity or similarity to (SEQ ID NO: 1)

MPASSPFLLAPKGPPGNMGGPVREPALSVALWLSWGAALGAVACAMALLTQ

QTELQSLRREVSRLQGTGGPSQNGEGYPWQSLPEQSSDALEAWENGERSRK

RRAVLTQKQKKQHSVLHLVPINATSKDDSDVTEVMWQPALRRGRGLQAQGY

GVRIQDAGVYLLYSQVLFQDVTFTMGQVVSREGQGRQETLFRCIRSMPSHP

DRAYNSCYSAGVFHLHQGDILSVIIPRARAKLNLSPHGTFLGFVKL.

In certain embodiments, APRIL is in the growth medium at a concentration of greater than $0.001 \times 10^{-3}\%$, $0.002 \times 10^{-3}\%$, $0.003 \times 10^{-3}\%$, $0.004 \times 10^{-3}\%$, $0.005 \times 10^{-3}\%$, $0.007 \times 10^{-3}\%$, $0.010 \times 10^{-3}\%$, $0.020 \times 10^{-3}\%$, $0.030 \times 10^{-3}\%$, $0.050 \times 10^{-3}\%$, $0.10 \times 10^{-3}\%$, $0.20 \times 10^{-3}\%$, $0.30 \times 10^{-3}\%$, $0.50 \times 10^{-3}\%$, $1.0 \times 10^{-3}\%$, $1.5 \times 10^{-3}\%$, $2.0 \times 10^{-3}\%$, 0.001%, 0.002%, 0.003%, 0.004%, 0.005%, 0.007%, 0.010%, 0.020%, 0.030%, 0.050%, 0.10%, 0.20%, 0.30%, 0.50%, 1.0%, 1.5%, 2.0%, by weight.

In response to injury, inflammatory cells such as neutrophil granulocytes and macrophages secrete a number of cytokines, most notable of which are the interleukins IL-1, IL-6 and IL-8, and TNFα. "IL-6" refers to the Interleukin-6 protein. IL-6 signals through a cell-surface type I cytokine receptor complex consisting of the ligand-binding IL-6Ra chain (CD126), and the signal-transducing component gp130 (CD130). IL-6 is thought to be involved in the activation of the immune system, regenerative processes, and regulation of metabolism.

In certain embodiments, a growth medium disclosed herein comprises exogenously added IL-6, fragment, or variant thereof. In certain embodiments, the variant has greater than 30, 40, 50, 60, 70, 80, 85, 90, 95, 96, 97, 98 or 99% identity or similarity to isoform 1 (SEQ ID NO: 2)

MNSFSTSAFGPVAFSLGLLLVLPAAFPAPVPPGEDSKDVAAPHRQPLTSSE

RIDKQIRYILDGISALRKETCNKSNMCESSKEALAENNLNLPKMAEKDGCF

QSGFNEETCLVKIITGLLEFEVYLEYLQNRFESSEEQARAVQMSTKVLIQF

LQKKAKNLDAITTPDPTTNASLLTKLQAQNQWLQDMTTHLILRSFKEFLQS

SLRALRQM.

In certain embodiments, the variant has greater than 30, 40, 50, 60, 70, 80, 85, 90, 95, 96, 97, 98 or 99% identity or similarity to isoform 2 (SEQ ID NO: 3),

CESSKEALAENNLNLPKMAEKDGCFQSGFNEETCLVKIITGLLEFEVYLEY

LQNRFESSEEQARAVQMSTKVLIQFLQKKAKNLDAITTPDPTTNASLLTKL

QAQNQWLQDMTTHLILRSFKEFLQSSLRALRQM.

In certain embodiments, IL-6 is in the growth medium at a concentration of greater than $0.001\times10^{-3}$%, $0.002\times10^{-3}$%, $0.003\times10^{-3}$%, $0.004\times10^{-3}$%, $0.005\times10^{-3}$%, $0.007\times10^{-3}$%, $0.010\times10^{-3}$%, $0.020\times10^{-3}$%, $0.030\times10^{-3}$%, $0.050\times10^{-3}$%, $0.10\times10^{-3}$%, $0.20\times10^{-3}$%, $0.30\times10^{-3}$%, $0.50\times10^{-3}$%, $1.0\times10^{-3}$%, $1.5\times10^{-3}$%, $2.0\times10^{-3}$%, 0.001%, 0.002%, 0.003%, 0.004%, 0.005%, 0.007%, 0.010%, 0.020%, 0.030%, 0.050%, 0.10%, 0.20%, 0.30%, 0.50%, 1.0%, 1.5%, 2.0%, by weight.

Sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q.

As used herein a "growth medium" or "media" refers to a composition that contains components, such as vitamins, amino acids, inorganic salts, a buffer, and a fuel, e.g., acetate, succinate, and/or a saccharide, that support the growth and maintenance of cell lines. Components in the growth medium may be derived from blood serum or the growth medium may be serum-free. The growth medium may optionally be supplemented with albumin, lipids, insulin and/or zinc, transferrin or iron, selenium, ascorbic acid, and an antioxidant such as glutathione, 2-mercaptoethanol or 1-thioglycerol.

As used herein the term "allogeneic" with regard to comparing cells capable of and/or secreting antibodies and mesenchymal stromal/stem cells (MSCs) refers to cells that are genetically dissimilar because they are not derived from the same person, e.g., the antibody secreting cells and the mesenchymal stromal/stem cells (MSCs), which provide for proteins secreted from mesenchymal stromal/stem cells (MSCs) in a growth media, are not both derived from the same person. Cells derived from the same person are designated as "syngeneic."

An "antigen" is any substance, e.g. a polypeptide or polysaccharide, which causes an immune system of an animal to produce an antibody that specifically binds to the antigen. "Specifically binds" refers to the ability of an antibody to recognize and bind the antigen, e.g., mature, full-length or partial-length target polypeptide, such that its affinity (as determined by assays) or its neutralization capability (as determined by assays) is at least 10 times as great, but optionally 50 times as great, 100, 250, or 500 times as great, or even at least 1000 times as great as the affinity or neutralization capability of the same for any other or other random molecule, e.g. peptide or polypeptide, due to interacts with the antigen binding domain. The term "antigen binding domain" or "antigen binding region" refers to that portion of the antibody molecule that contains the amino acid residues that interact with an antigen and confer its specificity and affinity for the antigen. In an antibody, the antigen-binding domain is commonly referred to as the "complementarity-determining region, or CDR."

The term "epitope" refers to that portion of any molecule capable of being recognized by and bound by a specific binding agent, e.g. an antibody, at one or more of the binding agent's antigen binding regions. Epitopes usually consist of chemically active surface groupings of molecules, such as for example, amino acids or carbohydrate side chains, and have specific three-dimensional structural characteristics as well as specific charge characteristics. Epitopes as used herein may be contiguous or non-contiguous.

The term "variable region" or "variable domain" refers to a portion of the light and/or heavy chains of an antibody, typically including approximately the amino-terminal 120 to 130 amino acids in the heavy chain and about 100 to 110 amino terminal amino acids in the light chain. The variable regions typically differ extensively in amino acid sequence even among antibodies of the same species. The variable region of an antibody typically determines the binding and specificity of each particular antibody for its particular antigen. The variability in sequence is concentrated in those regions referred to as complementarity-determining regions (CDRs), while the more highly conserved regions in the variable domain are called framework regions (FR). The CDRs of the light and heavy chains contain within them the amino acids which are largely responsible for the direct interaction of the antibody with antigen, however, amino acids in the FRs can significantly affect antigen binding/recognition as discussed herein infra.

The term "light chain" when used in reference to an antibody collectively refers to two distinct types, called kappa (k) or lambda (l) based on the amino acid sequence of the constant domains.

The term "heavy chain" when used in reference to an antibody collectively refers to five distinct types, called alpha, delta, epsilon, gamma and mu, based on the amino acid sequence of the heavy chain constant domain. The combination of heavy and light chains give rise to five known classes of antibodies: IgA, IgD, IgE, IgG and IgM, respectively, including four known subclasses of IgG, designated as $IgG_1$, $IgG_2$, $IgG_3$ and $IgG_4$.

Long-Term In Vitro Human Plasma Cell Survival System

Plasma cells are the main source of both protective and pathogenic autoantibodies and as such, they represent the effector arm of the humoral system. From a cellular standpoint, ASC are a heterogeneous compartment comprised of multiple subsets with distinct surface phenotype and different participation in short-lived and long-lived antibody responses. Long-lived antibodies provide persistent serological memory and account for protection against past pathogens but are also responsible for the persistence of pathogenic auto- and allo-antibodies even after therapeutic B cell depletion. Therefore, a precise understanding of the survival properties of human ASC populations and of their relative participation in different immune responses bears substantial implications for the manipulation of human antibody responses in health and disease. However, the fragility of ASC ex vivo and their accelerated spontaneous in vitro cell death under normal culture conditions have precluded a systematic investigation of human ASC. These properties impede reliable evaluation of ASC numbers in multicenter clinical studies that require the storage and/or transport of blood samples to specialized referral laboratories. Finally, the confluence of all these factors imposes major limitations for ASC repertoire analysis and the generation of monoclonal antibodies of pre-determined antigenic specificity. The latter limitation is particularly problematic given that ASC specific for most microbial and self-antigen represent less than 1% of all BM short-lived or LLPC.

An in vitro cell-free human plasma cell culture system disclosed herein is promoted by factors derived from the BM microenvironment that naturally supports long-term survival of PC in vivo. BM MSC are an essential part of the in vitro survival system and that their effect is mediated through a soluble secretome in the absence of cell-cell contact. These conditions eliminate the need for feeder cells thereby establishing a simple cell-free system capable of sustaining short- and long-term ASC culture. Moreover, the efficiency of allogeneic MSC secretomes eliminates the challenging and time consuming requirement of obtaining concomitant BM aspirates and blood ASC from every individual analyzed. Instead, large preps of MSC secretome can be obtained from allogeneic samples and stored frozen until needed thereby increasing experimental simplicity and throughput and minimizing experimental variability.

The actual identity of the specific components of the MSC secretome responsible for PC survival remains unknown. However, proteins, lipids, or even carbohydrates are all possible candidates that should be amenable to analysis. APRIL imparts a survival advantage when added to the MSC secretome and may enhance Ig production on a per cell basis. APRIL-enhanced survival was observed for up to 56 weeks, a timeframe that strongly suggests an important role for this cytokine in the maintenance of human long-lived plasma cells. Of note, the lack of benefit of APRIL alone suggests that it acts synergistically in concert with other secretome factors. An in vivo, the amount of APRIL produced by BM MSC that may be physiologically supplemented from other local sources of this cytokine including eosinophils or neutrophils.

Experiments indicate evidence for a survival benefit induced by hypoxic conditions that recapitulate the distinct hypoxic BM microenvironment. Hypoxia enhanced PC survival above and beyond the benefit imparted by the addition of APRIL to the MSC secretome. However, and in contrast to other conditions tested, the effects of hypoxia were only noted after 7 days in culture, a time frame that suggests the engagement of adaptation programs.

The in vitro system disclosed herein can be adapted for multiple needs since it provides quick ASC functional recovery, short-term ASC survival (days) and long-term ASC cultures (for week to months). Functional recovery would alleviate a major limitation of human ASC studies, namely the small cell numbers that are generally available for analysis. Moreover, there commonly is a major discrepancy between functional readouts and the number of input ASC. This problem is perhaps best illustrated by Elispot studies in which frequently the number of antibody spots would account for a relatively small fraction of input ASC thereby raising concerns about the purity of the test population.

This problem is created by decreased ASC function secondary to sorting stress which is consistently reversed within the first 24 hours of culture to provide 250-500% functional recovery. Improved functionality can be obtained with un-supplemented secretome, a practical and less expensive approach to documenting the purity of ASC samples while also enhancing the ability to study small cell numbers. In turn, enhanced function and improved survival over 1-2 weeks can be supported by the combination of the secretome and APRIL. These conditions are well suited to generate bulk ASC cultures to measure the presence of protective or pathogenic reactivities and to maintain single cell ASC cultures to identify antigen specific ASC for the generation of monoclonal antibodies of pre-determined reactivity.

Ideal conditions for long-term cultures would consist of the MSC secretome and APRIL under hypoxic conditions. These cultures would enable the measurement and isolation of low-frequency ASC and provide the experimental basis to study basic mechanisms of LLPC generation and maintenance.

Systems disclosed herein can also expedite human monoclonal antibody generation. Conventional approaches rely on direct ex vivo cloning of antigen-specific ASC present in high frequency in the circulation after antigenic challenge through either infection or immunization. However, these approaches require careful timing of the blood samples for ASC isolation during acute illness which may not be possible in some diseases. A relatively low throughput also limits the applicability of this method for the isolation of rare antigen-specific ASC that may represent <0.1% of available cells. However, this goal is greatly facilitated by enrichment of antigen-specific ASC prior to antibody cloning. Unfortunately, a lack of surface antibody expression on many ASC limits selection and requires the production of enough antibody for in vitro detection of their antigenic reactivity.

Corti, D., et al., report using IL-6 to support single ASC cultures from highly enriched blood ASC after vaccination or infection to isolate broadly-reactive influenza antibodies. Science 333, 850-856 (2011). Their overall efficiency with VH and VL gene transcript was 15-40%. System disclosed herein compares favorably as it can deliver much higher efficiencies for total IgG and influenza-specific ASC cultures with nearly 90-100% VH and VL RNA recovery. Thus, it is possible to interrogate pre-determined neutralizing antibodies from single BM plasma cell cultures for further therapeutic monoclonal antibody engineering within weeks.

The BM microniche needed to maintain blood ASC survival using a cell-free reproducible in vitro plasma cell survival system is described. The survival of circulating ASC isolated from the blood requires a hypoxic environment with paracrine survival factors from BM stroma (MSC) and exogenous APRIL.

Methods disclosed herein reduce the need to generate monoclonal antibodies to understand specificities at a single cell level. For example, during emerging pandemics, to understand cross-reactivity, one can measure antibody cross-reactivity in healthy and vulnerable populations. In addition on is able to interrogate memory B cells at a single cell level. Single memory B cells are sorted, proliferate in culture and put in our plasma cell survival system to have enough antibody secreted from the memory B cell to understand its specificity. Monoclonal antibodies can be generated by selecting specificities prior to generating monoclonal antibodies. One can interrogate the memory B cell compartment on a single cell basis and can enumerate the number of memory B cells that are Dengue and Zika cross-reactive.

In addition, one can enumerate the cellular origins of pathogenic donor specific antibodies (DSA) in patients awaiting solid organ transplants and those who are suffering rejection. Using therapies one can eliminate plasma cell subsets (blood, BM, etc.) and memory B cell compartments. Thereafter, one can test for the development of donor specific antibodies (DSA).

This system could also offer tools for precision medicine as it relates to multiple myeloma (MM), a highly lethal ASC tumor with heterogeneous response to a growing number of therapeutic candidates. Yet, similar to normal ASC, primary multiple myelomas are notoriously difficult to maintain in culture thereby precluding susceptibility testing to a variety of chemotherapeutic agents. Our system can sustain primary myeloma tumors ex vivo from patients and potentially offer personalized approaches to MINI single and combination therapies.

Environments for In Vitro Culturing of Antibody Secreting Cells

In certain embodiments, relates to growth media and environments for in vitro culturing of cells that produce or are capable of producing antibodies. In certain embodiments, the media comprises IL-6, fibronectin, and typically a saccharide. In certain embodiments, the disclosure contemplates cell culture compositions comprising IL-6 and fibronectin that are derived from proteins secreted from mesenchymal stromal/stem cells (MSCs). In certain embodiments, the disclosure contemplates enclosures comprising culture compositions disclosed herein that are in ambient air or optionally in an environment wherein oxygen is absent or at a low concentration.

In certain embodiments, the enclosure comprises ambient air or is optionally sealed from the atmosphere wherein the amount of oxygen is less than 10%, 5.0%, 2.5%, 2.0%, 1.5%, 1.0%, 0.5%, or 0.1% by volume.

In certain embodiments, the proteins secreted from mesenchymal stem cells are derived from extracting the proteins from a group of mesenchymal stromal/stem cells (MSCs) or are derived from replicating or non-replicating mesenchymal stromal/stem cells (MSCs) or irradiated mesenchymal stromal/stem cells (MSCs) in the growth medium. In certain embodiments, the mesenchymal stem cells are grown to near confluence and irradiated.

In certain embodiments, the growth medium further comprises exogenously added APRIL, IL-6, and/or fibronectin. In certain embodiments, the growth media comprises the proteins interleukin-6 (IL-6) and fibronectin that are exogenously added. In certain embodiments, the growth media further comprises an exogenously added buffering agent, amino acids and vitamins.

In certain embodiments, the growth media further comprises exogenously added blood. Typically, the blood is manipulated so that cells, platelets and/or clotting factor have been removed or are substantially absent, e.g., less than 5%, 3%, 2% or 1% by weight.

In certain embodiments, the disclosure relates to methods of culturing cells that are capable of producing antibodies comprising mixing cells capable of producing antibody with a cell growth medium disclosed herein. In certain embodiments, the cells that are capable of producing antibodies are plasma cells or antibody-secreting cells (ASCs). In certain embodiments, the plasma cells have surface molecules in a pattern wherein no or low levels of CD19 are expressed, CD138 is expressed, and CD38 is expressed in higher levels than CD138.

In certain embodiments, the culturing is done under conditions such that cells that are capable of producing and/or secreting antibodies survive or secret antibodies for more than 3, 4, 5, 6, 7, 8, 9, 10, 15, 20, 25, 30, 35, 40, 45, 50, 55, or 56 days.

In certain embodiments, the disclosure relates to composition comprising cells made by the process disclosed herein.

In certain embodiments, the disclosure contemplates the use of or secretions of allogeneic mesenchymal stromal/stem cells (MSCs) or syngeneic mesenchymal stromal/stem cells (MSCs). In certain embodiments, the disclosure contemplates that the growth medium does not contain syngeneic mesenchymal stromal/stem cells (MSCs). In certain embodiments, the disclosure contemplates that the cells capable of producing and/or antibody secreting cells have no cell to cell contact with the allogeneic mesenchymal stromal/stem cells (MSCs) or syngeneic mesenchymal stromal/stem cells (MSCs). In certain embodiments, the disclosure contemplates that the survival media comprises a product derived from the secreted products of allogeneic mesenchymal stromal/stem cells (MSCs). In certain embodiments, allogeneic mesenchymal stromal/stem cells (MSCs) or syngeneic mesenchymal stromal/stem cells (MSCs) are bone marrow derived mesenchymal stromal/stem cells (MSCs).

In certain embodiments, the disclosure contemplates a growth media disclosed herein having one or more of the following components in the RPMI 1640 and R10 medium at, about, or greater than those provided in the tables herein. The term "about" refers to having more or less not exceeding 10, 20, 30, 40 or 50% by weight.

RPMI 1640 Medium contains the reducing agent glutathione and vitamins. RPMI 1640 Medium contains biotin, vitamin B12, and PABA. In addition, the vitamins inositol and choline are present. RPMI 1640 Medium does not contain substantial amounts of proteins, lipids, or growth factors. RPMI 1640 Medium is commonly supplemented with 1-5% or 5-10% Fetal Bovine Serum (FBS). RPMI 1640 Medium uses a sodium bicarbonate buffer system (2.0 g/L).

TABLE 1

Components RPMI 1640 Medium

| | Molecular Weight | Concentration (mg/L) |
|---|---|---|
| Amino Acids | | |
| Glycine | 75.0 | 10.0 |
| L-Arginine | 174.0 | 200.0 |
| L-Asparagine | 132.0 | 50.0 |
| L-Aspartic acid | 133.0 | 20.0 |
| L-Cystine 2HCl | 313.0 | 65.0 |
| L-Glutamic Acid | 147.0 | 20.0 |
| L-Glutamine | 146.0 | 300.0 |
| L-Histidine | 155.0 | 15.0 |
| L-Hydroxyproline | 131.0 | 20.0 |
| L-Isoleucine | 131.0 | 50.0 |
| L-Leucine | 131.0 | 50.0 |
| L-Lysine hydrochloride | 183.0 | 40.0 |
| L-Methionine | 149.0 | 15.0 |

TABLE 1-continued

Components RPMI 1640 Medium

| | Molecular Weight | Concentration (mg/L) |
|---|---|---|
| L-Phenylalanine | 165.0 | 15.0 |
| L-Proline | 115.0 | 20.0 |
| L-Serine | 105.0 | 30.0 |
| L-Threonine | 119.0 | 20.0 |
| L-Tryptophan | 204.0 | 5.0 |
| L-Tyrosine disodium salt dihydrate | 261.0 | 29.0 |
| L-Valine | 117.0 | 20.0 |
| Vitamins | | |
| Biotin | 244.0 | 0.2 |
| Choline chloride | 140.0 | 3.0 |
| D-Calcium pantothenate | 477.0 | 0.25 |
| Folic Acid | 441.0 | 1.0 |
| Niacinamide | 122.0 | 1.0 |
| Para-Aminobenzoic Acid | 137.0 | 1.0 |
| Pyridoxine hydrochloride | 206.0 | 1.0 |
| Riboflavin | 376.0 | 0.2 |
| Thiamine hydrochloride | 337.0 | 1.0 |
| Vitamin $B_{12}$ | 1355.0 | 0.005 |
| i-Inositol | 180.0 | 35.0 |
| Inorganic Salts | | |
| Calcium nitrate ($Ca(NO_3)_2$ $4H_2O$) | 236.0 | 100.0 |
| Magnesium Sulfate ($MgSO_4$) (anhyd.) | 120.0 | 48.84 |
| Potassium Chloride (KCl) | 75.0 | 400.0 |
| Sodium Bicarbonate ($NaHCO_3$) | 84.0 | 2000.0 |
| Sodium Chloride (NaCl) | 58.0 | 6000.0 |
| Sodium Phosphate dibasic ($Na_2HPO_4$) anhydrous | 142.0 | 800.0 |
| Other Components | | |
| D-Glucose (Dextrose) | 180.0 | 2000.0 |
| Glutathione (reduced) | 307.0 | 1.0 |
| Phenol Red | 376.4 | 5.0 |
| R10 medium | | |

500 mL, RPMI 1640 medium
  55 mL Heat-inactivated fetal calf serum (FCS)
  5 mL, L-glutamine (200 mM solution)
  5 mL, Penicillin/streptomycin (10,000 U per mL and 10 mg per mL)
  5 mL 1 M HEPES buffer Other contemplated components in these growth medium include ascorbic acid, L-alanine, zinc sulfate, human transferrin, albumin, insulin, ammonium metavanadate, cupric sulfate, manganous chloride, sodium selenite, ethanolamine, and sodium pyruvate.

The term "saccharide" refers to multi-hydroxylated hydrocarbons which predominantly form one or more cyclic five and/or six membered nonaromatic oxygen containing cyclic isomers in aqueous solutions. The term includes monosaccharides, disaccharides, or polysaccharides such as glucose, dextrose, fructose, lactose, mannose, sorbitol, or sucrose.

The term, "irradiation" of the cells, refers to exposing the cells to a γ-irradiation source. In certain embodiments, one irradiates the cells at about or more than or 50, 60, 70, 75 or 76.6 rad/minute (e.g. ~0.766 Gy/minute) and do so for at or more than 20, 25, 30, 35 or 40 minutes. 3,064 rad, or 30.64 Gy).

Antibody Secreting Cell (ASC) Survival Human plasma cells (PCs), or antibody-secreting cells (ASCs), produce antibodies (Abs) that provide protection from infections. As terminally-differentiated cells, these cells rapidly die in conventional ex vivo cultures. This hinders in vitro studies of these 1 immune cells. It may be that bone marrow (BM)-derived mesenchymal stromal cells (MSCs) "microniches" where long-lived PCs reside, prolong ASC survival in vitro. To test this hypothesis, peripheral blood (PB) ASCs were cultured on BM-MSCs and their survival and Ab production were assessed by ELISpot and ELISA assays. ASCs died within 1-3 days in conventional cultures; however, when co-cultured with BM-MSCs, they survived and continuously secreted Abs for greater than 63 days. MSC-ASC cell-cell contact was not necessary. BM-MSC secretome supported ASC survival similarly. APRIL alone did not support ASC survival, but APRIL together with BM-MSC secretome promoted survival and Ab secretion of cultured ASCs. In addition, ASCs cultured with APRIL in BM-MSC secretome in hypoxia (2.5% 02) showed enhanced cell survival compared to those in normoxic conditions (for greater than 56 days). The human secretome from BM-MSCs supports long-term (more than a month) ex vivo survival and Ab production of human PB ASCs. These paracrine effects were further enhanced by exogenous APRIL and hypoxic stress.

Circulating ASC upon arrival to the hypoxic BM microniche require the paracrine survival factors from the BM stroma and APRIL from eosinophils or neutrophils to maintain survival. Serendipitously methods were developed to understand additional mechanisms of plasma cell differentiation and maintenance. These can be used as tools for basic plasma cell biology central to advance fields of vaccinology, oncology, autoimmunity, allergy, and transplantation.

The BM microenvironment is important for plasma cells (PCs). Experiments indicate that amidst the sundry collection of cells, the BM-MSC is necessary but not sufficient for human plasma cell survival. Human PCs in both in vitro and animal models suggested that MSC effects were mediated by both cell-to-cell contact and soluble factors. Proximity of the MSC to the plasma cell is paramount with local concentration of survival factors but cell-to-cell contact is not necessary. Thus, allogeneic human MSC secretome provided a full collection of plasma cell survival factors.

Although the BM-MSC are necessary, they alone were not sufficient to sustain long-term plasma cell survival. The synergistic effect of one cytokine, APRIL, together with the BM MSC secretome prolonged survival as well as increased Ig production per cell as shown by the size of the ELISpots. These studies indicate that MSC do not readily provide APRIL in the BM microniche or at least not in meaningful abundance. Finally, plasma cells in the MSC secretome in hypoxia were maintained longer than in normoxia. Thus, the MSC survival media with APRIL in hypoxia enhanced long-lived survival of blood ASC for almost 2 months and likely could be sustained longer. These differences were not immediate but with survival curves diverging after 7 days depicted intrinsic changes of the plasma cell imparted by the unique features and special secreted factors provided by the BM microniche.

Plasma cells are terminally differentiated professional antibody secreting factories. Yields of viable human ASC are diminished after surface staining in the cold combined with sorting under high-pressure flow systems. However, culture conditions disclosed herein increased cell numbers of IgG ASC on 1-2 days. Although, this phenomenon could have been due to proliferation of blood ASC, no proliferation is detected by BrdU labeling of Ki67+ cells. Thus, Ki67+ staining of these cells are a result of recent proliferation and not ongoing cell division. Thus, FACS sorted ASC are re-awakened from a "non-secreting" to a fully active "secreting" phenotype. Hence, immunoglobulin secretion is not entirely constitutive but is modulated during stress and revived during nutrient rich states.

Nearly all ASC in the blood are positive for Ki67 staining which was originally interpreted as ongoing division of plasmablasts even after upregulation of BLIMP-1. However, BLIMP-1 expression has been shown to repress c-myc and other genes involved in cell cycle progression and cell division suggesting plasma cell differentiation programs are distinct from proliferation. ASC positive for Ki67+, a marker of ribosomal RNA localized to the nucleus during interphase, are not actively proliferating but rather have undergone recent proliferation.

APRIL is secreted by eosinophils and neutrophils which are found in the BM. Eosinophils are important in LLPC generation and maintenance. APRIL played an additive role in long-term plasma cell survival in the presence of the BM-MSC secretome demonstrating that APRIL was not provided by the BM-MSC. Proximity of eosinophils and plasma cells was thought to be essential due to the importance of cell-to-cell contact. However, exogenous APRIL within the BM microsite is important for long-term ASC survival and eosinophil-plasma cell contact was not necessary. Eosinophils have also been shown to be important in the generation of IgA plasma cells. However, a higher frequency of IgG plasma cells are found in the BM LLPC compartment (CD19−CD38hiCD138+) compared to IgA plasma cells. Interestingly, in vitro BM microniche cultures, IgA ASC were not "revived" on days 1-2. Even with APRIL and the BM secretome, IgA ASC gradually waned after 2 weeks. Thus, this in vitro BM plasma cell survival system is optimal for IgG plasma cells and a different potpourri of factors will likely be central for IgA plasma cell survival.

The circulating ASC are easily found in blood after immunization and infection and many undergo apoptosis since serum antibody peak by one month and quickly decline within 2-3 months. The sustained secondary serum antibody kinetics are likely due to those circulating ASC that have migrated to survival sites in the human BM in proximity to the MSC and APRIL enriched zones. Our studies demonstrate that the BM microniche not only supports plasma cells but likely alters its phenotype to adapt to hostile hypoxic sites. Our RNA transcriptome analysis of ex vivo BM plasma cell populations (both short-lived and long-lived) suggest upregulation of hypoxia adaptation pathways, altered metabolic pathways, and autophagy pathways.

Reaction of the GC is important in generating LLPC, however, it is unclear if a unique subset of post-GC circulating ASC are intrinsically programmed to be LLPC such as CD138+ subset of blood ASC. One model proposes that all circulating ASC have the potential to become LLPC, provided they undergo each sequential differentiation step such as upregulation of CD38, CD27, CD138, and eventual loss of CD19 to become LLPC.

As an example, ASC from the patient who received the PSV23 had only a frequency of 70% of total ASC survival on day 8 in MSC secretome and APRIL compared to other vaccine responses with over 180% survival on day 6-8. Moreover, the high frequency of plasma cells was sustained for 14 days for most other vaccines. Typically, PSV23 requires frequent re-immunization every 5 years due to a rapid decline of antibody titers. The swift deterioration of ASC in our in vitro cultures could reflect the lack of LLPC maintenance after this particular vaccine. In contrast, ASC after tetanus, MMR (a live attenuated vaccine), and trivalent influenza vaccination showed higher ASC frequencies on day 7-8 and maintained to day 14. Interestingly, tetanus and MMR are vaccines with greater durability requiring boosters every 10 to 20 years due to prolonged half-lives. Hence, the durability of ASC survival at 2 weeks using our in vitro BM culture system provides possible effective novel assays to define vaccine biomarkers of longevity.

The specific survival factors secreted by the BM MSC are not well characterized. Proteins, lipids, or even carbohydrates are all possible candidates. The role of IL-6 is important since inhibition show decreases in ASC survival in culture. However, the IL-6 receptor expression was reduced on human LLPC compared to other BM plasma cell subsets. Extracellular matrix proteins such as heparin sulfate, collagen, laminin, and fibronectin may prove to be important along with additional cytokines such as IL-10, IL-5, and APRIL.

Experimental

Antibody Sequencing of Human Long-Lived Plasma Cells (LLPC)

Experiments using MSCs for culturing cells are reported in WO 2016/201077. Cell-free secretomes of BM MSCs and exogenous cytokines under normoxic and hypoxic conditions as an in vitro system is able to sustain human ASC survival for several months. This system enables the study of human long-lived plasma cells (LLPC) generation and maintenance. Moreover, it allows efficient interrogation of well-defined ASC populations to precisely identify the sources of protective and pathogenic serum antibodies in specific human diseases. By extending these methods to single cell cultures, one is able to select rare antigen specific clones and provide VH and VL sequences within one week to expedite human monoclonal antibody generation.

In Vitro Characterization of Antigen-Specific Blood and BM Plasma Cell Responses Microbial-specific ASC are highly enriched in the blood after vaccination and during acute infection with antigen-specific frequencies ranging from 30 to 90% of total ASC 20-23. A in vitro culture system was used to analyze antigen-specific ASC responses both at the population and single cell level. To that end, CD19+CD27hiCD38hi ASC sorted from healthy adults 7-day after tetanus immunization were cultured with MSC secretome+APRIL for 21 days to allow for the accumulation of secreted antibody. This approach resulted in the generation of abundant total IgG and vaccine-specific IgG, both at similar concentrations (>200 ng/mL) (FIG. 1A). Similar results were generated with ASC obtained after influenza immunization in 28-day ASC cultures (110-190 ng/mL and 70-180 ng/mL for total IgG and influenza-specific IgG, respectively). In contrast, no tetanus- or influenza-specific IgG was detected in similar ASC cultures from a healthy asymptomatic non-vaccinated adult despite ample amounts of total IgG (>200 ng/mL). These results are consistent with high enrichment for anti-gen-specific ASC responses after vaccination in the absence of significant bystander effects.

Figure 1B:
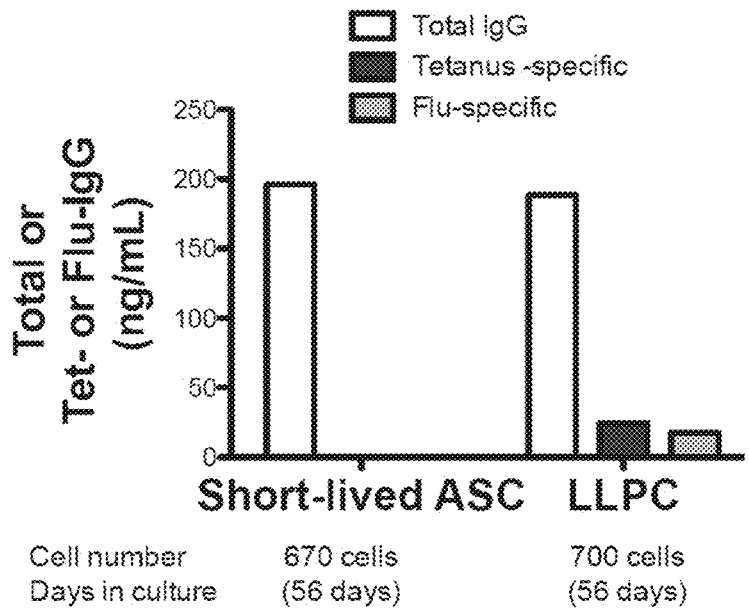
FIG. 1B shows data on BM plasma cell subsets isolated from a healthy adult. Total IgG, tetanus-specific, and influenza-specific IgG from 670 pop B plasma cells: shortlived (CD19+CD38hiCD138+) and 700 pop D plasma cells: long-lived (CD19-CD38hiCD138+) of 56 day cultures.

This approach was also used to interrogate the antigenic specificity of different BM ASC subsets based on the observations that the human BM ASC compartment is heterogeneous and is comprised of different subpopulations. Bona fide BM LLPC responsible for decades long anti-viral serological memory are restricted to a distinct population characterized by a CD19−CD38hiCD138+ phenotype, and the frequency of viral-specific cells within the LLPC compartment ranges from 0.1-2% of all IgG producing cells. See Halliley et al. Long-Lived Plasma Cells Are Contained within the CD19(−)CD38(hi)CD138(+) Subset in Human Bone Marrow. Immunity 43, 132-145 (2015). Accordingly, 700 LLPC and 670 short-lived ASC (CD19+CD38hiCD138+) were sorted from the BM of healthy subjects with known past history of tetanus and flu immunization and no recent flu immunization or exposure. The different fractions were then cultured and tested for antibody production and specificity as above. As shown in FIG. 1B, tetanus and influenza-specific IgG antibodies were detected in the LLPC cultures (at 25 and 18 ng/mL, respectively) but not in the short-lived ASC cultures. Thus, the in vitro culture system allows for easy interrogation of the antibody specificity of distinct ASC populations even as it pertains to low-frequency responses.

Figure 1C:
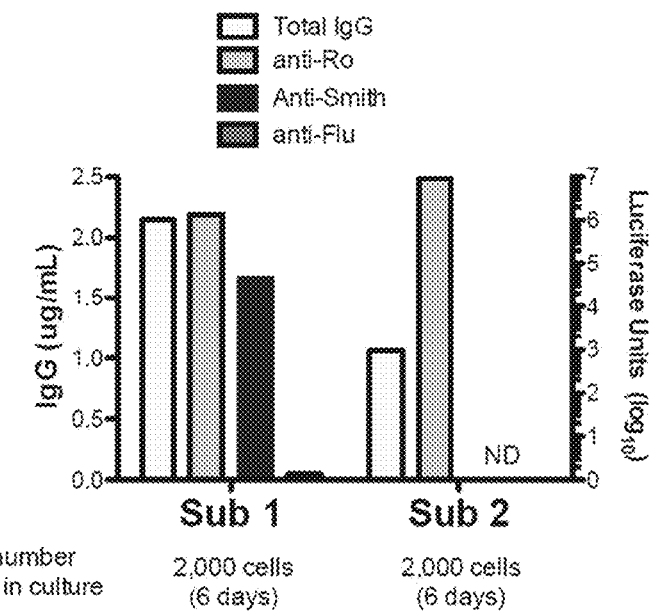
FIG. 1C shows data on blood ASC isolated from two SLE patients and anti-Ro and anti-Sm are detected by LIPS from 2,000 ASC per well for 6 days.

Having demonstrated feasibility for detection of protective anti-microbial antibodies, methods were used to evaluate the origins of serum pathogenic autoantibodies in the circulating ASC. ASC (CD19+CD27hiCD38hi) (2,000) were cultured from the blood of two patients with Systemic Lupus Erythematosus (SLE) for 6 days in MSC secretome and APRIL and tested for anti-Ro and anti-Smith (Sm) autoantibodies using a Luciferase Immunoprecipitation Systems (LIPS) that allows highly sensitive and quantitative measurements. Both patients had high serum titers for anti-Ro and anti-Sm. An overabundance of total IgG was detected from blood ASC cultures in both patients (FIG. 1C). Interestingly, in the presence of active disease, subject 1 had anti-Ro and anti-Sm antibodies detectable from the cultures (and no influenza-specific antibodies); however, subject 2, with inactive disease had only anti-Ro (not anti-Sm) antibodies in the ASC cultures suggesting differential circulation of pathogenic autoantibody ASC in SLE disease, possibly on the basis of disease activity.

Using the System to Interrogate ASC at a Single Cell Level

Figure 1D:
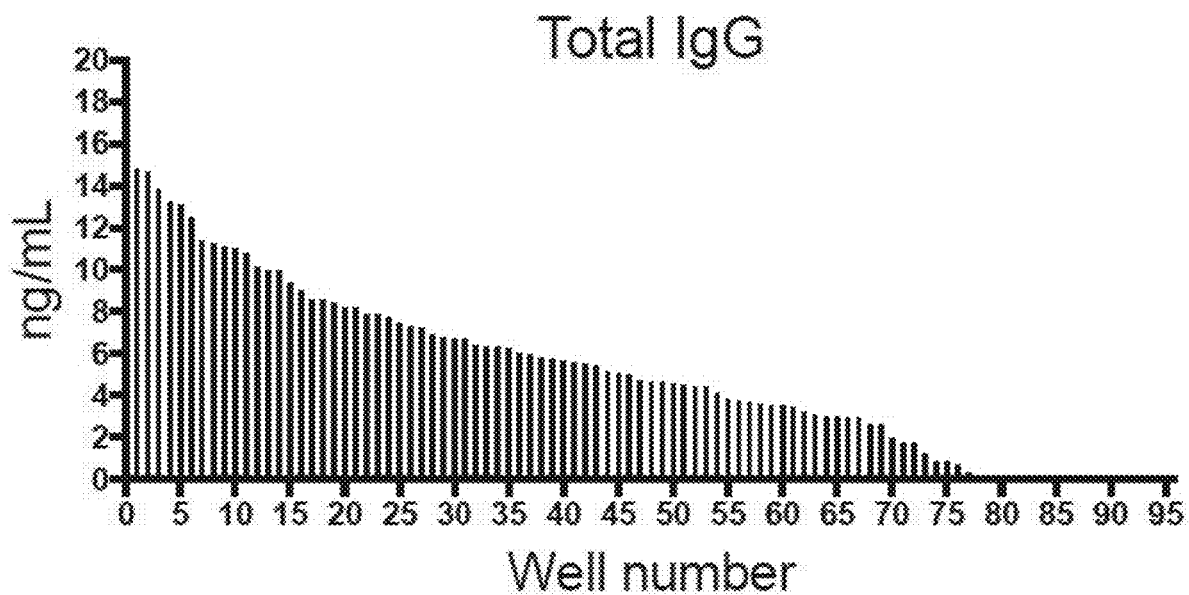
FIG. 1D shows single FAC sorted ASC from an adult after influenza vaccination were cultured for 6 days in the MSC secretome and APRIL. Total IgG in ng/mL were measured by ELISA from each well containing a single cell.
Figure 1E:
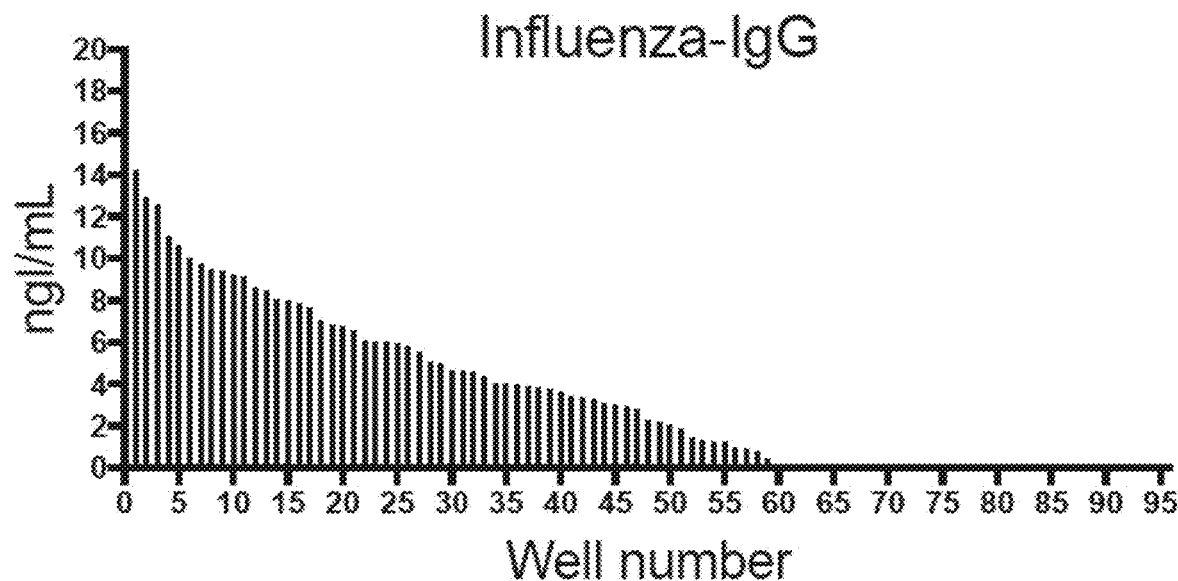
FIG. 1E shows data on total TIV-specific IgG.

Cultures we utilized to interrogate ASC at a single cell level. To do so, individual CD19+CD27hiCD38hi ASC were sorted from the blood after influenza vaccination and cultured for 6 days with the MSC secretome and APRIL. Total IgG was easily detected in 77 of 96 single ASC cultures (80%) and TIV-IgG was identified in 59 of 96 single ASC cultures (61%) (FIGS. 1D and 1E). Given the frequency of antigen-specific IgG producing cells typically induced by vaccination (30-90%) and that IgA ASC can also be induced in response to systemic immunization, these numbers demonstrate a very high efficiency of single ASC cultures. Quantitatively, total IgG secretion ranged 3 to 148 pg/cell/day or 0.3-15 ng/mL and influenza-IgG concentrations were similar after 6-day cultures. Again, these numbers are consistent with a highly efficient single antigen-specific ASC response after vaccination.

Figure 1F:
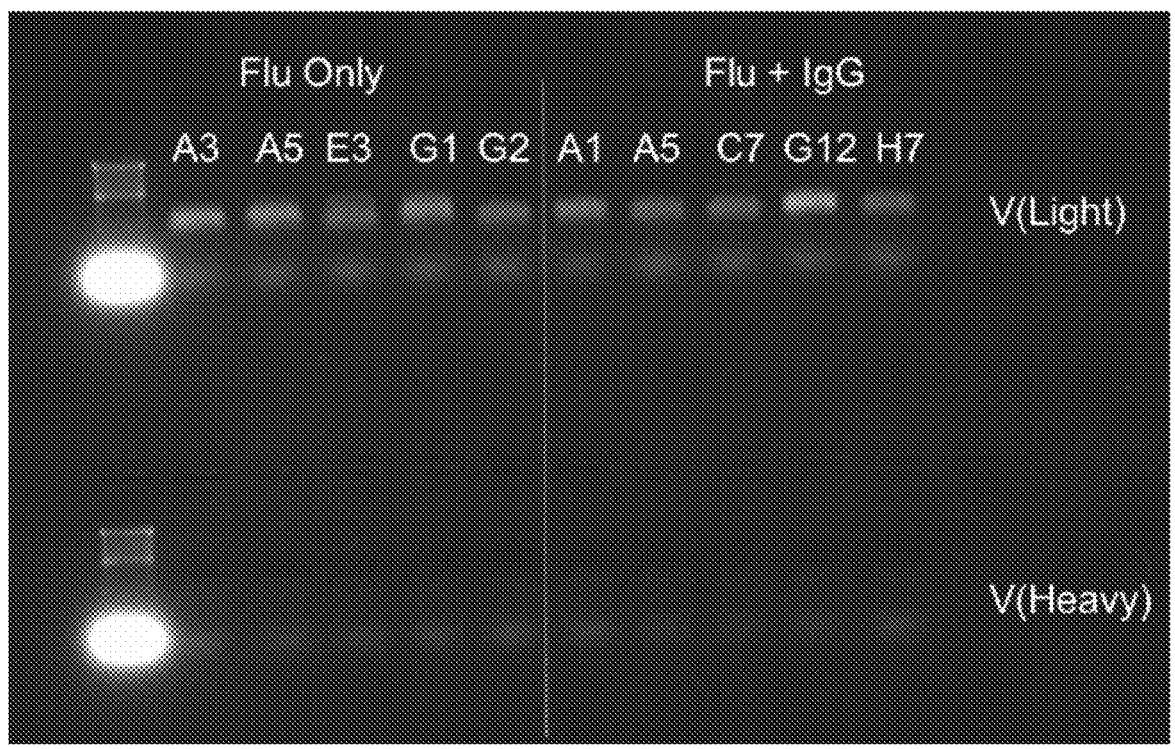
FIG. 1F shows VH and VL RNA isolation from influenza-specific IgG positive wells identified by six day single (CD19+CD27hiCD38hi) ASC cultures after influenza immunization. Efficiency is 90-100% of the selected clones (2 experiments).

Single ASC clones positive for influenza-specific IgG were selected and the heavy (VH) and light (VL) chains were amplified (FIG. 1F). The in vitro plasma cell culture system can rapidly identify antigen-specific single ASC clones and provide VH and VL sequences within a week. Therefore, this approach enables both repertoire analysis and quick generation of monoclonal antibodies pre-selected for antigenic specificity, affinity and/or functional properties.

Interrogation of Memory B Cells at a Single Cell Level Using the System

Figure 2A:
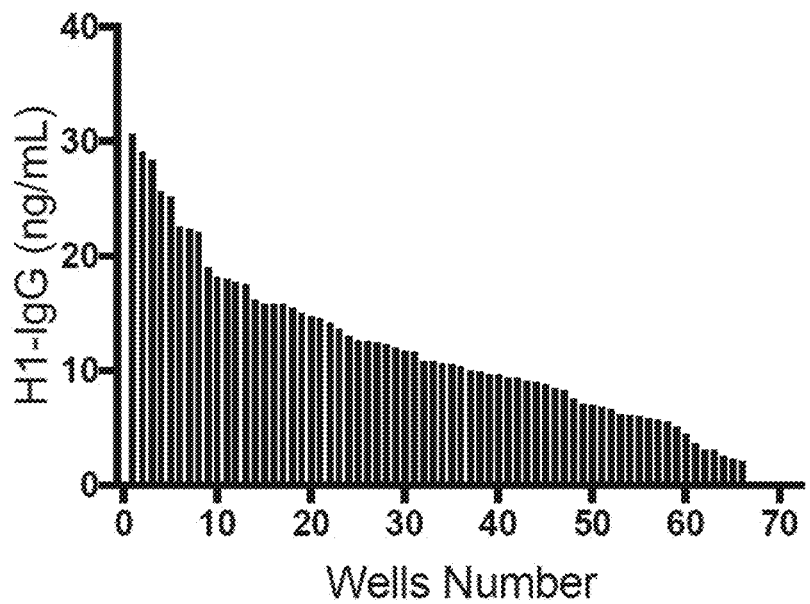
FIG. 2A shows data on H1-IgG of individual H1-tetramer-positive memory B cells cultures. Single cell cultures of H1-tetramer-positive and H1-tetramer-negative memory B cells. H1-tetramer-positive and H1-tetramer-negative memory B cells (CD19+CD27+IgD−) were individually FAC sorted from an adult on month after influenza virus infection and cultured for 7 days with R848, IL-2, and IL-21. From days 8-12, MSC secretome and APRIL were added for an additional 5 days. H1-IgG and H3-IgG were measured by ELISA from the supernatants of single memory B cell cultures.
Figure 2B:
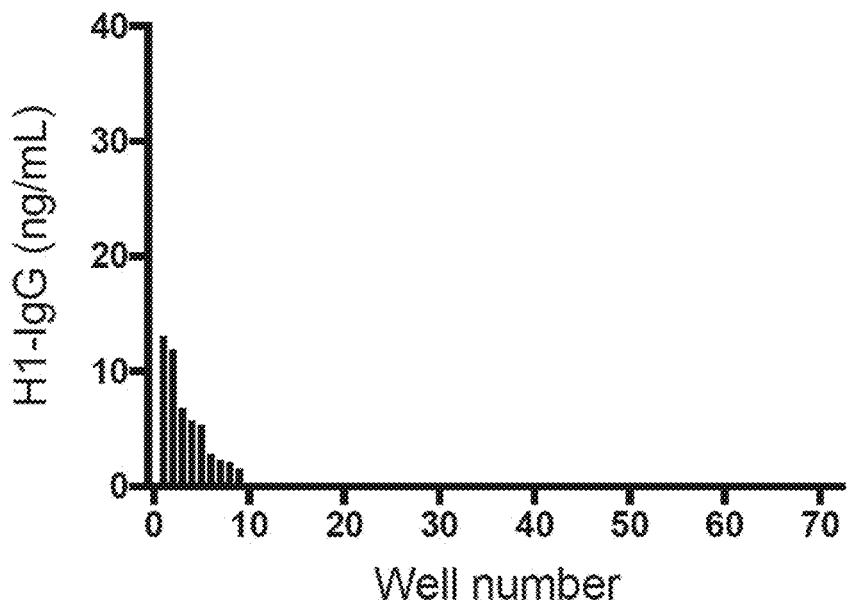
FIG. 2B shows data on H1-IgG of individual H1-tetramer-negative memory B cells cultures.
Figure 2C:
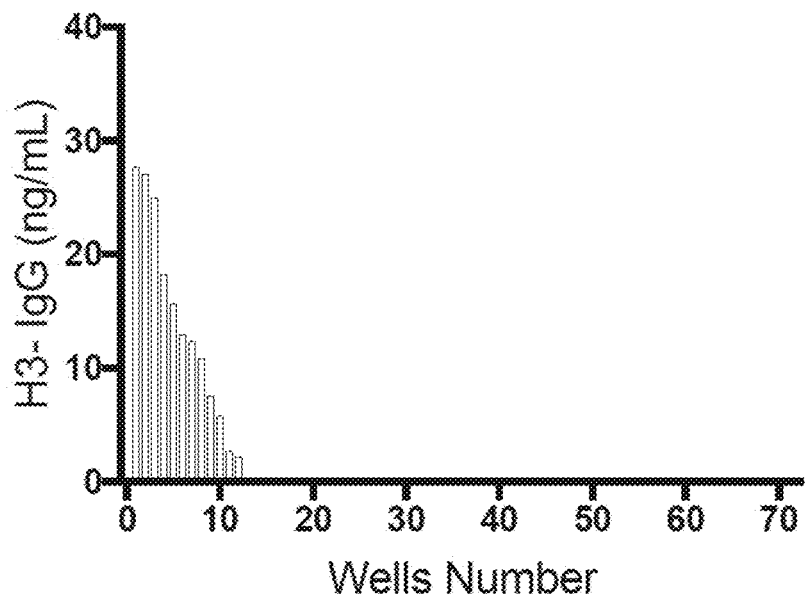
FIG. 2C shows data on H3-IgG of individual H1-tetramer-positive memory B cells cultures.
Figure 2D:
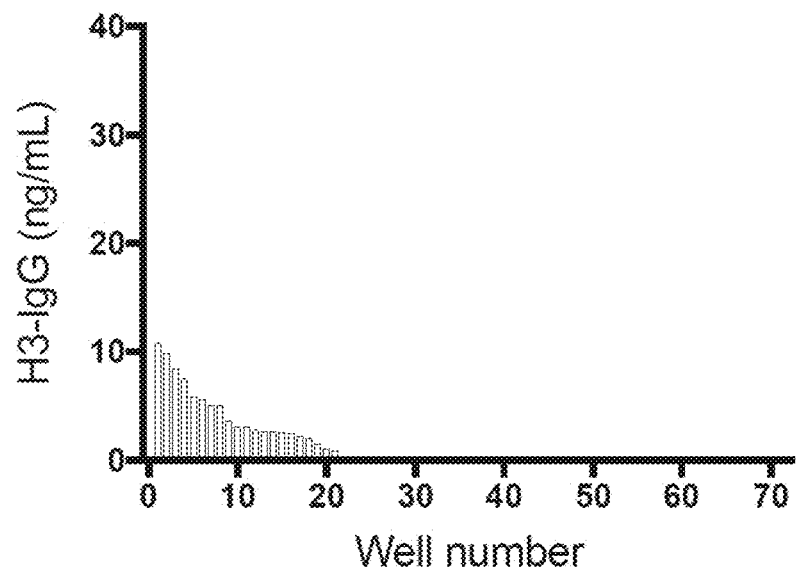
FIG. 2D shows data on H3-IgG of individual H1-tetramer-negative memory B cells cultures.

Identification of antigen-specific memory B cells has been a major challenge in the field due to variability of antigen labeling methods. Thus, fluorescently labeled recombinant hemagglutinin (HA) B cell tetramers from influenza H1N1 A/CA/07/09 (H1) were generated. To validate the specificity of the H1-B cell tetramer on human memory B cells, the culture system was modified to interrogate the specificity of individual memory B cells rather than recombinantly manufacturing hundreds of monoclonal antibodies from sorted H1-tetramer-positive B cells. To this end, H1-tetramer-positive and H1-tetramer-negative memory B cells were single cell sorted from an adult 28 days after influenza virus infection and memory B cells were cultured in R848, IL-2, and IL-21 for 7 days then added the MSC secretome and APRIL for the remaining 5 days. Single H1-Tet positive memory B cell cultures were tested for H1-IgG and H3-IgG (H3N2 A/Texas/50/2012) specificity (FIG. 2A, FIG. 2C). Of the 72 H1-Tet positive B cells, 66 of single memory cell cultures were positive for H1-IgG while 9/72 of the H1-Tet negative B cell controls were positive (FIG. 2A, FIG. 2B). Similarly, of the 72 H1-tetramer-positive B cells, only 12 were positive for H3 while 21/72 H1-tetramer-negative memory B cells demonstrated reactivity for H3 (FIG. 2C, 2D). This higher H3 frequency of the H1-tetramer-negative B cells may have been due to natural enrichment of H3 memory B cells in patients with an influenza (H3N2) viral infection. Direct applications of the in vitro plasma cell survival system can be used to efficiently interrogate or screen memory B cells at a single cell level without generating monoclonal antibodies.

BM-Derived Mesenchymal Stromal Cells (BM-MSCs) and Secretome.

BM-MSCs were derived from bone marrow aspirates of healthy donors. BM mononuclear cells (MNCs) were isolated by Ficoll-Hypaque (GE Healthcare) or Lymphocyte Separation Medium (LSM; Cellgro/Corning) density-gradient centrifugation. Adherent cells were classified as primary BM-MSCs and further propagated ex vivo for subsequent uses, which were generally between their $3^{rd}$ and 8th passages. Irradiated BM-MSCs (iMSC) were exposed to γ-irradiation (30.64 Gy). Supernatants were harvested from BM-MSC monolayer cultures. Pooled supernatants were centrifuged to remove floating cell debris.

Isolation of Peripheral Blood Mononuclear Cells (PBMCs) and ASC.

PBMCs were separated from freshly collected PBL samples by Ficoll-Hypaque (GE Healthcare) or Lymphocyte Separation Medium (LSM; Cellgro/Corning) density-gradient centrifugation. T cells and monocytes were removed by CD3 and CD14 beads and flow through stained with the following panel (human CD3-PECy5.5, human CD14-PE-Cy5.5 (Life Tech); human CD19-PE-Cy7, human IgD-FITC, human CD27-APC-eFluor780, human CD38-v450, and human CD138-APC (BD Biosciences) The ASC populations (CD19+CD27hiCD38hi) were generally ~85-99% pure, as assessed by flow cytometric re-analysis of post-sort cells.

Establishment of In Vitro Culture Systems for Human Blood and BM ASCs.

BM MSCs as feeder (co-cultures on adherent monolayer) were co-cultured in 96-well flatbottom cell culture plates or transwells (0.4 μm pore polycarbonate insert membrane of 96-well plates (Corning/Sigma)) in 37° C. in a humid, 5% $CO_2$, 95% air (20% O2) incubator or in hypoxic culture conditions (2.5% O2) at 37° C. in a modular incubator chamber (Billups-Rothenberg) that was infused with a preanalyzed gas mixture containing 2.5% O2, 5% $CO_2$, and 92.5% N2 (AirGas). The initial input ASC numbers for each culture varied (~100 to 3,082 cells per well) depending upon total post-sort cells. The same numbers of ASC were also reserved for day 0 IgG Elispots. In MSC secretome media, ASC alone were cultured with factors for specified days. For MSC free cultures or control cultures, RPMI with 10% fetal bovine serum (R10) were used. Cells were harvested on designated days and IgG Elispot assays were performed. Supernatants collected from the cultures were used for IgG ELISAs. The blood or BM ASC survival and function were assessed by Elispot assays, and their output values were expressed as the percentage of IgG secreting ASCs relative to day 0. Exogenous factors included a variety of cytokines and growth factors, IL-5, IL-6, APRIL, BAFF, IFNg, (R&D), IL-21 (Peprotech), bFGF (Thermofisher Scientific) and CXCL12 (Rockland) were added to cultures at day 0 with ASCs. The final concentrations of the added factors, which were optimized based on titrated experiments and the manufacturer's recommendations.

Single or Bulk ASC Cultures:

Bulk ASC from blood (CD19+CD27hiCD38hi) and BM (pop B: CD19+CD138+CD38hi and pop D: CD19−CD138+hiCD38hi) were and cultured. Single ASC (CD19+CD27hiCD38hi) were also sorted on the FACS ARIA and cultured for 6 days in culture in 96-well plates. Supernatants from bulk or individual single cell cultures were assayed by ELISA for total IgG, influenza-, and tetanus-specific IgG. Ninety six-well flat-bottom ELISA microplates (Nunc/Corning) were pre-coated overnight at 4° C. with goat anti-human IgG or 2015-2016 quadrivalent influenza vaccine (2 µg/mL or 1 µg/mL, respectively, in PBS; 100 µL/well). After washing and blocking, diluted single cell supernatants were incubated for 1 hr at RT. Plates were washed and secondary goat anti-human IgG-alkaline phosphatase, (Jackson ImmunoResearch Lab) added. Wells were detected using Blue-Phos Microwell Phosphatase Substrate System (KPL) at RT for 15-60 minutes and analyzed at 650 nm.

LIPS Assay for Ro and Smith.

LIPS was performed in a 96-well plate format. For each test 15-20 uL of SLE cultured supernatants were used. Additional sera dilutions were also performed for total IgG. Plates were washed and light units (LU) were measured in a Berthold LB 960 Centro luminometer (Berthold Technologies, Bad Wildbad, Germany) with coelenterazine mix (Promega, Madison, WI, USA).

Single Cell RT-PCR Amplification of VH and VL:

After removal of the culture supernatants from the in vitro plasma cell survival system, single ASC were place in RNA lysis buffer and stored at −80 C until cDNA isolation. Briefly, cDNA was synthesized in a total volume of 20 µL/well in the original 96-well-sorting plate using iScript cDNA Synthesis kit (Bio-Rad). IgH, Igλ, and Igκ V gene transcripts were amplified independently by nested PCR using 4 µl cDNA. All PCR reactions were performed in 96-well plates in a total volume of 40 µl/well containing 50 nM each primer, 250 µM each dNTP (Fermentas, Glen Burnie, MD), and 0.25 U HotStar Taq DNA polymerase (Qiagen, Valencia, CA). PCR amplification of Ig L and Ig H chains was accomplished using literature techniques. See Tiller, T., et al. Efficient generation of monoclonal antibodies from single human B cells by single cell RT-PCR and expression vector cloning. J Immunol Methods. 2008, (1-2): 112-124; Wrammert, J., et al. Rapid cloning of high-affinity human monoclonal antibodies against influenza virus. Nature 453, 667-671 (2008); Smith et al. Rapid generation of fully human monoclonal antibodies specific to a vaccinating antigen. Nature Protocols 4, 372-384 (2009); and Wrammert et al. Broadly cross-reactive antibodies dominate the human B cell response against 2009 pandemic H1N1 influenza virus infection. J Exp Med, 208, 181-193 (2011).

Production of Influenza Proteins and B Cell Tetramers.

The extracellular coding sequences of HA (H1) from A/CA/07/09 HA18-524 (accession number: C3W5X2) and HA (H3) from A/TX/50/12 HA17-525 (accession number: R4L1D1) were synthesized in frame with the human CD5 signal sequence upstream and the GCN4 isoleucine zipper trimerization domain downstream (GeneArt, Regensburg, Germany). These cDNAs were fused in frame with either a 6×HIS tag or an AviTag at the C-terminus and cloned into the pCXpoly+ mammalian expression vector. Constructs encoding HA-6×HIS and HA-AviTag were co-transfected using 293fectin into FreeStyle™ 293-F Cells (ThermoFisher Scientific) at a 2:1 ratio. Transfected cells were cultured in FreeStyle 293 Expression Medium media for 3 days and the supernatant was recovered by centrifugation. Recombinant HA molecules were purified by FPLC using a HisTrap HP Column (GE Healthcare), and eluted with 250 mM of imidazole. Purified HA and NP proteins were biotinylated by addition of biotin-protein ligase (Avidity, Aurora, CO). Biotinylated proteins were then tetramerized with fluorochrome-labeled streptavidin (Prozyme, Hayward, CA). Labeled tetramers were purified by size exclusion on a HiPrep 16/60 Sephacryl S-300 column (GE Healthcare, Piscataway, NJ).

Single Memory Cell Cultures:

PBMCs were isolated from freshly collected blood samples. Cells were re-suspended in Neuraminidase (Sigma-Aldrich) 5 u/mL at a concentration of 1:100 per 1×10$^7$ cells and incubated for 30 minutes at 37° C. prior to staining. Cells were subsequently stained with the following panel (human CD3-PE-Cy5.5, human CD14-PE-Cy5.5 (Life Tech); human CD19-PE-Cy7, human IgD-FITC, human CD27-APC-eFluor780, human CD38-v450, and HA (CA7Tetramer)-APC (BD Biosciences). The memory B cell populations CD19+CD27+CD38− HA (CA7) Tetramer-positive and CD19+CD27+CD38− HA (CA7) Tetramer-negative were sorted in single cell plates containing the MSC secretome and APRIL (200 ng/mL), R848 (Invitrogen) (1 ug/mL), IL-2 (Peprotech) (10 ng/mL), and IL-21 (Peprotech) (100 ng/mL). Cells were then incubated at 37° C. for 7 days. Then, the media was diluted 1:2 incubated for 5 additional days at 37° C. Supernatants from single cell cultures were then assayed by ELISA for total IgG, H1 and H3 secretion. 96-well flat-bottom ELISA microplates (Nunc/Corning) were pre-coated overnight at 4° C. with goat anti-human IgG or H1 and H3 antigens (2 µg/mL, 10 ug/mL, and 10 ug/mL, respectively, in PBS; 100 µL/well).

The invention claimed is:

1. A method of identifying cells that produce antibodies that bind to an antigen comprising
isolating antibody secreting cells from a sample, providing isolated single antibody secreting cells;
mixing the isolated antibody secreting cells with secretions of allogeneic mesenchymal stromal/stem cells and exogenously added A-proliferation-inducing ligand (APRIL) under conditions such that isolated antibody secreting cells replicate providing replicated antibody secreting cells; and
identifying antibodies that specifically bind to the antigen being secreted from the cells indicating the presence of antigen binding antibody secreting cells in the sample.

2. The method of claim 1 wherein mixing the isolated antibody secreting cells with secretions of allogeneic mesenchymal stromal/stem cells and exogenously added A-proliferation-inducing ligand (APRIL) is under hypoxic conditions.

3. The method of claim 1, wherein the sample is blood, bone marrow, or product derived therefrom.

4. The method of claim 1, wherein the antibody secreting cells have a cell surface profile of CD19(−), CD38(hi), and CD138(+).

5. The method of claim 1, wherein the antibody secreting cells have a cell surface profile of CD19+, CD27hi, and CD38hi.

6. The method of claim 1, wherein the antigen is a vaccine antigen or autoimmune antigen.

7. A method of producing a hybridoma that produces antibodies that bind to an antigen comprising:
- isolating antibody secreting cells from a sample providing separated single antibody secreting cells in a plurality of separate areas,
- mixing the separated single antibody secreting cells with secretions of allogeneic mesenchymal stromal/stem cells and exogenously added A-proliferation-inducing ligand (APRIL) under conditions such that separated single cells replicate providing replicated homogenous antibody secreting cells; and
- identifying homogenous antibody secreting cells that produce antibodies that specifically bind to the antigen; and
- fusing a homogenous antibody secreting cell identified to produce antibodies that specifically bind the antigen with an immortalized cell providing hybridoma cells that produce antibodies that specifically bind to the antigen.

* * * * *